(12) United States Patent
Larsen

(10) Patent No.: US 9,611,198 B2
(45) Date of Patent: Apr. 4, 2017

(54) METHOD FOR CATALYST REGENERATION

(75) Inventor: Ryan Larsen, Yorba Linda, CA (US)

(73) Assignee: M-I L.L.C., Houston, TX (US)

( * ) Notice: Subject to any disclaimer, the term of this patent is extended or adjusted under 35 U.S.C. 154(b) by 502 days.

(21) Appl. No.: 14/113,366

(22) PCT Filed: Apr. 17, 2012

(86) PCT No.: PCT/US2012/033925
§ 371 (c)(1),
(2), (4) Date: Feb. 20, 2014

(87) PCT Pub. No.: WO2012/145310
PCT Pub. Date: Oct. 26, 2012

(65) Prior Publication Data
US 2014/0155671 A1 Jun. 5, 2014

Related U.S. Application Data

(60) Provisional application No. 61/476,520, filed on Apr. 18, 2011.

(51) Int. Cl.
| | |
|---|---|
| *B01J 38/06* | (2006.01) |
| *B01J 38/16* | (2006.01) |
| *B01J 23/94* | (2006.01) |
| *B01J 23/92* | (2006.01) |
| *C07C 7/148* | (2006.01) |
| *B01J 23/96* | (2006.01) |
| *C01B 17/04* | (2006.01) |
| *B01J 38/04* | (2006.01) |

(52) U.S. Cl.
CPC .......... *C07C 7/14858* (2013.01); *B01J 23/92* (2013.01); *B01J 23/94* (2013.01); *B01J 23/96* (2013.01); *B01J 38/06* (2013.01); *B01J 38/16* (2013.01); *C01B 17/0465* (2013.01); *B01J 38/04* (2013.01); *Y02P 20/584* (2015.11)

(58) Field of Classification Search
None
See application file for complete search history.

(56) References Cited

U.S. PATENT DOCUMENTS 4,002,720 A * 1/1977 Wheelock .............. B01D 53/04
423/230
4,233,276 A 11/1980 D'Souza et al.
(Continued)

FOREIGN PATENT DOCUMENTS

| | | |
|---|---|---|
| EP | 1920836 A1 | 5/2008 |
| WO | 00/02645 | 1/2000 |

(Continued)

OTHER PUBLICATIONS

Examination Report issued in AU2012245668 on Jan. 27, 2015, 2 pages.
(Continued)

*Primary Examiner* — Tam M Nguyen
(74) *Attorney, Agent, or Firm* — Sara M. Hinkley

(57) ABSTRACT

The various embodiments relate to a system and method for regenerating a direct oxidation catalyst that coverts $H_2S$ to elemental S. One embodiment of the method comprises regenerating a direct oxidation catalyst by contacting the direct oxidation catalyst with steam.

6 Claims, 2 Drawing Sheets

(56) References Cited

U.S. PATENT DOCUMENTS

| | | | |
|---|---|---|---|
| 4,332,781 A | | 6/1982 | Lieder et al. |
| 4,391,735 A | | 7/1983 | Busse |
| 4,552,746 A | * | 11/1985 | Kettner ............. B01D 53/8612 423/224 |
| 4,795,726 A | | 1/1989 | Schaper et al. |
| 5,442,108 A | | 8/1995 | Kawajiri et al. |
| 5,763,350 A | * | 6/1998 | Immel ................ B01D 53/8603 502/307 |
| 5,851,944 A | * | 12/1998 | Luebke ................... B01J 38/48 502/22 |
| 6,017,507 A | | 1/2000 | Nougayrede et al. |
| 6,099,819 A | * | 8/2000 | Srinivas ............ B01D 53/8612 423/242.1 |
| 2007/0006780 A1 | * | 1/2007 | Mesters ............. C01B 17/2016 106/815 |
| 2008/0260611 A1 | | 10/2008 | Aderhold et al. |

FOREIGN PATENT DOCUMENTS

| | | |
|---|---|---|
| WO | 0002645 A1 | 1/2000 |
| WO | 2012145310 A1 | 10/2012 |

OTHER PUBLICATIONS

Search Report issued in EP12774875.4 on Jan. 26, 2015, 6 pages.
International Search Report and Written Opinion issued in PCT/US2012/033925 on Jan. 13, 2015, 12 pages.
International Search Report and Written Opinion of PCT/US2012/033925 dated Sep. 25, 2012.
Eurasian Official Action for corresponding Eurasian Application No. 201391539/31, dated Sep. 14, 2015, 4 pages.
First Mexican Office Action for corresponding Mexican Application No. MX/a/2013/012175, dated Sep. 22, 2015, 4 pages.
Second Mexican Office Action for corresponding Mexican Application No. MX/a/2013/012175, dated Jan. 14, 2016, 5 pages.
Eurasian Official Action for corresponding Eurasian Application No. 201391539/31, dated Sep. 19, 2016, 4 pages.
Australian Patent Examination Report for corresponding Application No. 2016200470, dated Jan. 27, 2016, 5 pages.
Canadian Patent Examination Report for corresponding Application No. 2,833,274 dated Apr. 1, 2015, 3 pages.

* cited by examiner

METHOD FOR CATALYST REGENERATION

FIELD OF THE INVENTION

Embodiments disclosed herein generally relate to the field of catalysts for oxidation of hydrogen sulfide to sulfur and water.

BACKGROUND OF INVENTION

Hydrogen sulfide ($H_2S$) is commonly found in natural gas wells and may also be produced in oil refining or other industrial processes. Because hydrogen sulfide increases corrosion and may be toxic in sufficient quantities, hydrogen sulfide content should be reduced to appropriate levels. An accepted method of reducing hydrogen sulfide content is the oxidation of hydrogen sulfide to sulfur and water. The sulfur product is considered benign in comparison to alternatives such as sulfur dioxide ($SO_2$), the product of burning hydrogen sulfide and a precursor to acid rain.

The Claus process is the state-of-the-art process for oxidizing hydrogen sulfide to convert it to sulfur and water. The Claus process is a two-step process. In the first step, a large quantity of the elemental sulfur is recovered in a furnace, and about one third of the remaining $H_2S$ is oxidized to $SO_2$. In the second step, the remaining $H_2S$ and the $SO_2$ are reacted in a Claus reactor to form sulfur according to the reaction:

$$2H_2S + SO_2 \rightarrow 2H_2O + 3S$$

Unfortunately, the gas fed to the Claus process must have a relatively high concentration of $H_2S$ gas to be efficiently incinerated in the furnace step. Also, the gas treated in a Claus process must have low amounts of hydrocarbons, which can interfere with the Claus reaction and generate other sulfur species, such as COS and $CS_2$. As a result, an $H_2S$-containing gas typically must be treated in an amine unit to first separate and concentrate the $H_2S$. Thus, the Claus process is generally economical only for large scale operations.

Direct oxidation catalysts that promote the oxidation of $H_2S$ to sulfur and water in a single step are one alternative to the multistep Claus process. Direct oxidation is effective at lower concentrations of $H_2S$. So, $H_2S$ separation in an amine unit is not necessary. Despite its advantages over the Claus process, direct oxidation is rarely used because the catalyst life is too short and attempts to regenerate the catalyst have failed.

Accordingly, there exists a need for a system and method for effectively regenerating the direct oxidation catalysts.

SUMMARY OF INVENTION

In one aspect, the embodiments disclosed herein relate to a method for regenerating a direct oxidation catalyst. In one embodiment, the method may comprise contacting the direct oxidation catalyst with steam. In some embodiments, the direct oxidation catalyst may comprise at least one of titanium oxide, aluminum oxide, or mixtures thereof. The direct oxidation catalyst may further comprise a promoter metal oxide selected from a group consisting of oxides of Mn, Co, Cu, Nb, Mo, Tc, Ru, Rh, Hf, Ta, W, Au, La, Ce, Pr, Nd, Pm, Sm, Eu, Gd, Tb, Dy, Ho, Er, Tm, Yb, Lu and mixtures thereof. In some embodiments, direct oxidation catalyst to be regenerated was fouled by exposure to hydrocarbons and sulfur-containing compounds. In some embodiments, the steam may be high temperature steam having a temperature above 200° C.

In another aspect, the embodiments disclosed herein relate to a process for treating a gas stream. In one embodiment, the process comprises contacting a gas stream comprising hydrogen sulfide and at least one component with an oxygen-containing gas in the presence of a direct oxidation catalyst. The process may further comprise contacting the direct oxidation catalyst with steam to regenerate the direct oxidation catalyst.

In still another aspect, the embodiments disclosed herein relate to a system for treating a gas stream comprising hydrogen sulfide. In one embodiment, the system may comprise: at least one first direct oxidation reactor in fluid communication with the gas stream, the direct oxidation reactor comprising an oxygen source and a direct oxidation catalyst; and a steam source in fluid communication with the first direct oxidation reactor.

Other aspects and advantages of the invention will be apparent from the following description and appended claims.

DETAILED DESCRIPTION

Figure 1:
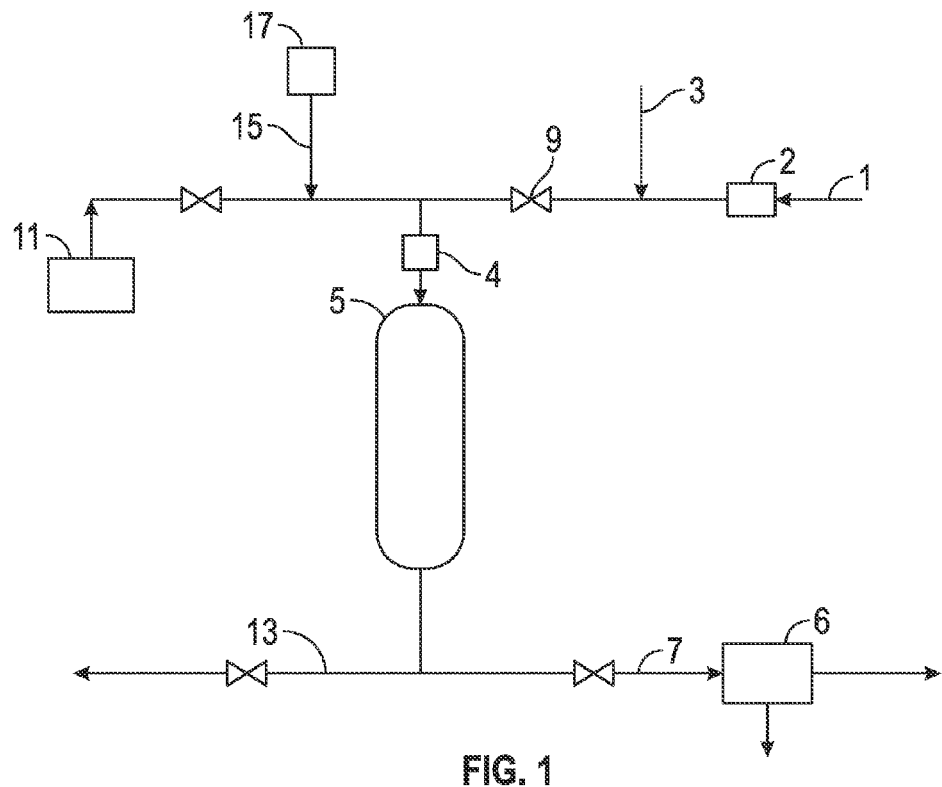
FIG. 1 is a schematic representation of a system in accordance with embodiments disclosed herein.

In one aspect, the embodiments disclosed herein relate to a method of regenerating a direct oxidation catalyst. A direct oxidation catalyst is a catalyst that promotes the direct oxidation of hydrogen sulfide ($H_2S$) with oxygen from air or enriched air to elemental sulfur (S) according to the following equation.

$$H_2S + \frac{1}{2}O_2 \rightarrow H_2O + S$$

The direct oxidation catalyst promotes the selectivity of this reaction to elemental sulfur over the side reaction to sulfur dioxide ($SO_2$). In the absence of an effective direct oxidation catalyst, the reaction of $H_2S$ with $O_2$ results in the formation of significant amounts of $SO_2$ and water.

In one embodiment, the direct oxidation catalyst comprises a metal oxide. In some embodiments the metal oxide is titanium oxide, aluminum oxide, or mixtures thereof. The direct oxidation catalyst may further comprise a second promoter metal oxide. These direct oxidation catalysts may be referred to as mixed metal oxide catalysts. In some embodiments, the promoter metal oxide may be selected from oxides of Mn, Co, Cu, Nb, Mo, Tc, Ru, Rh, Hf, Ta, W, Au, La, Ce, Pr, Nd, Pm, Sm, Eu, Gd, Tb, Dy, Ho, Er, Tm, Yb, Lu and mixtures thereof. In other embodiments, the promoter metal oxide may be selected from the group consisting of oxides of Nb, Mo, and Ce, and mixtures thereof. In one particular embodiment, the direct oxidation catalyst comprises titanium oxide ($TiO_2$), niobium oxide ($Nb_2O_5$) and molybdenum oxide ($MoO_3$). Further description and embodiments of direct oxidation catalysts can be found in U.S. Pat. No. 6,099,819, which is incorporated by reference as if fully set forth herein.

One drawback to using direct oxidation catalysts is that they typically foul when certain hydrocarbon compounds are present with the $H_2S$-containing gas being treated. These problematic hydrocarbons may include unsaturated hydrocarbons (such as ethylene) and high molecular weight hydrocarbons (>C4). The fouling occurs because deposits form on the catalyst leading to poor performance and/or deactivation of the catalyst. Even at extremely low levels, the hydrocarbon compounds can cause fouling. The problematic, deposit-forming hydrocarbons are found in most hydrocarbon sources. As a result, the fouling problem is so pervasive, that it has prevented direct oxidation catalysts from being adopted for $H_2S$ treatment in the oil and gas industry to this point.

Because of the unique nature of the fouling deposits, attempts to prevent the fouling or regenerate a fouled direct oxidation catalyst have been surprisingly unsuccessful. Without being bound to a particular theory, it is believed that the deposits are particularly difficult to remove because they may be formed of carbonaceous materials that are essentially vulcanized by the sulfur in the $H_2S$-containing gas, crosslinking and stabilizing the deposits. As a result, direct oxidation catalysts have only been successfully used to treat extremely clean gases having only minimal hydrocarbon content, such as gases containing nearly 100% $CO_2$. Attempts to prevent fouling by removing from the gas the compounds that form the deposits have been unsuccessful because they are cost prohibitive and/or not efficient enough to remove of all the deposit-causing compounds. In the past, attempts to remove the deposits from the catalyst were similarly unsuccessful. For example, even the most aggressive technique known, essentially burning the deposit with air at high temperatures (>300° C.) is not effective at regenerating the fouled direct oxidation catalyst without destroying the catalyst. High temperature air regeneration causes temperatures to rise uncontrollably in the reactor to about 875° C., which sinters the catalyst, massively reducing its surface area.

Referring to FIG. 1, embodiments of the system and method are shown. During the direct oxidation phase an $H_2S$-containing gas 1 and $O_2$-containing gas 3 are fed to a direct oxidation reactor 5. The direct oxidation reactor 5 contains the direct oxidation catalyst. In various embodiments, the direct oxidation reactor 5 may be a packed-bed type reactor. The $H_2S$-containing gas 1 may include some hydrocarbon compounds, such as unsaturated and high molecular weight hydrocarbons. In some embodiments, the source of the $H_2S$-containing gas may be natural gas, a refining process, gases associated with oil production, or the byproduct of a chemical synthesis process, a landfill, or water treatment operations. In some instances, the source of $O_2$-containing gas may be air or any other oxygen-containing gas.

In the direct oxidation reactor 5, the $H_2S$ and $O_2$ react in the presence of the direct oxidation catalyst, which promotes the selectivity of oxidizing the $H_2S$ to elemental sulfur over the side reaction oxidizing $H_2S$ to yield $SO_2$, total oxidation. The direct oxidation reaction is typically performed at temperatures elevated well above ambient temperature. In one embodiment, the temperature in the reactor 5 is controlled by heating $H_2S$-containing gas 1 in a heat exchanger 2. The $O_2$-containing gas 3 may be added to the heated $H_2S$-containing gas 1 and the combination is fed to a mixer 4, such as a static mixer. Additionally, the direct oxidation reactor itself may be heated and/or the $O_2$-containing gas may be heated. The temperature of the mixture of the $H_2S$-containing gas and the $O_2$-containing gas may be selected to optimize direct oxidation reaction's selectivity for producing S over $SO_2$ for the given conditions, e.g. the particular catalyst used and the levels of various constituents in the $H_2S$-containing gas. In addition, the temperature may be selected so that the temperature in the reactor is held high enough to avoid condensation of sulfur on the catalyst. In various embodiments, temperature in the reactor 5 may be heated to 100° C.-400° C.

Treated gas 7 exits the direct oxidation reactor 5. The treated gas 7 includes the sulfur product of the direct oxidation and the remaining constituents of the $H_2S$-containing gas, such as hydrocarbons and $CO_2$. The sulfur may be separated from the treated gas 7 in a condenser 6 by condensing the sulfur from treated gas 7.

While the direct oxidation reactor 5 is often referred to in the singular throughout the various embodiments, it should be understood that the term "reactor" may include multiple reactors operating in parallel or in series. The number of direct oxidation reactors operating in parallel may be chosen to accommodate the volume of gas to be treated. The operation of multiple direct oxidation reactors in series, may be necessary to achieve the desired overall reduction is $H_2S$ content. Optionally, sulfur may be condensed between the reactors or after the treated stream exits the last reactor in the series.

Over time, the direct oxidation catalyst fouls, becoming less effective at producing elemental sulfur. In some embodiments, fouling may be detected by monitoring the amounts of $SO_2$ generated in the direct oxidation reactor 5, which are present in the treated gas 7. The $SO_2$ levels in the treated gas 7 may be monitored by any number of $SO_2$ detectors known in the art.

The direct oxidation catalyst may be regenerated by contacting the catalyst with steam. In some embodiments, the catalyst to be regenerated is fouled by exposure to hydrocarbons, the $H_2S$-containing gas, condensed elemental sulfur and/or other sulfur-containing compounds. The hydrocarbons may be unsaturated hydrocarbons, high molecular weight hydrocarbons (>C4), or both. Steam regeneration may be performed at any point when it is considered useful or necessary. In various embodiments, steam regeneration is performed when a decrease in the catalyst's effectiveness is detected or after a pre-determined period of time. In one embodiment, the method comprises contacting the catalyst with high temperature steam at a temperature greater than 200° C. In another embodiment, the method comprises contacting the catalyst with steam above 310° C. In other embodiments, the steam is at 200° C.-400° C. In still other embodiments, the contact with steam occurs at 300° C.-400° C. Optionally, air or another oxygen source may be added to the steam used to regenerate the direct oxidation catalyst. In some embodiments, the amount of oxygen added to the steam may be less than 21% by volume.

In one embodiment, steam regeneration is performed by stopping the flow of $H_2S$-containing gas 1 to the direct oxidation reactor 5. This may be done using a control valve 9 or any other means, such as redirecting $H_2S$-containing gas 1 to another direct oxidation reactor. Steam is added to the direct oxidation reactor 5 from a steam source 11, such as a steam generator. The steam source may include a heat source thermally coupled to the steam source. The amount of time necessary for the steam to regenerate the fouled direct oxidation catalyst will vary. In some cases, 4 hours of steam flow to the direct oxidation catalyst may be sufficient time to regenerate the catalyst. In other cases, as long as 15 days or more may be necessary. The waste 13 from the steam regeneration process exits the direct oxidation reactor 5. Optionally, the progress and completion of the regeneration process may be evaluated by monitoring the total sulfur content and/or the carbon content in the waste 13. When the total sulfur content or the carbon content in the waste 13 are within acceptable limits or no longer detectable, the steam regeneration of the catalyst may be deemed complete.

Optionally, after the steam regeneration is complete, the direct oxidation catalyst may be contacted with an inert gas 15, such as nitrogen, from an inert gas source 17. The inert gas may serve to cool the direct oxidation catalyst and/or to purge the direct oxidation reactor 5 of any remaining steam or hydrocarbon condensates.

Figure 2:
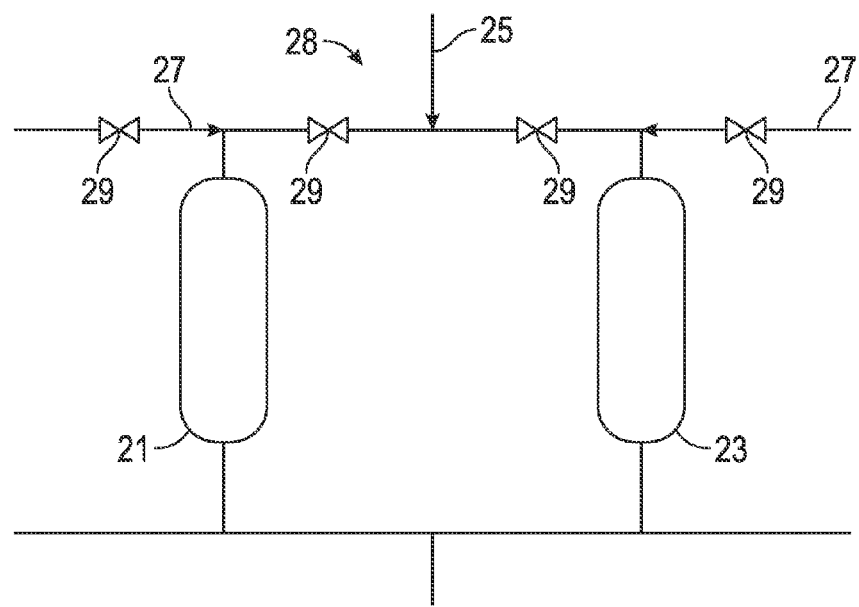
FIG. 2 is a schematic representation of a system in accordance with embodiments disclosed herein.

Referring to FIG. 2, an embodiment is shown wherein multiple direct oxidation reactors are used to create a continuous process. In this so-called "swing bed" arrangement, at least one first direct oxidation reactor 21 and at least one second direct oxidation reactor 23 are configured so that $H_2S$-containing gas 25 may be routed to either reactor. Steam 27 may also be routed to either reactor 21 or 23. In this configuration, $H_2S$-containing gas 25 may be routed to a direct oxidation reactor for treatment while steam 27 is routed to another reactor to regenerate the direct oxidation catalyst.

Routing the $H_2S$-containing gas, steam, oxygen, and/or other streams to the various reactors, condensers, and other may be performed in any manner know in the art. In some embodiments, a piping system 28 comprising the necessary valves 29 may be used to route the various streams to the various reactors.

In some embodiments, the direct $H_2S$ oxidation and catalyst regeneration process may be combined with a process for hydrolyzing carbonyl sulfide (COS). COS hydrolysis occurs in the presence of a catalyst according to following reaction:

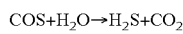

A number of catalysts are known to suitable for COS hydrolysis, including for example activated alumina. Because the products of COS hydrolysis include $H_2S$, treating the COS hydrolysis product in a direct oxidation reactor may be effective. In addition, when carbon monoxide (CO) is present in the feed gas to a direct oxidation reactor, COS may be formed in the direct oxidation reaction. Therefore in some embodiments, it may be useful to treat the effluent of the direct oxidation reactor with COS hydrolysis.

Figure 3:
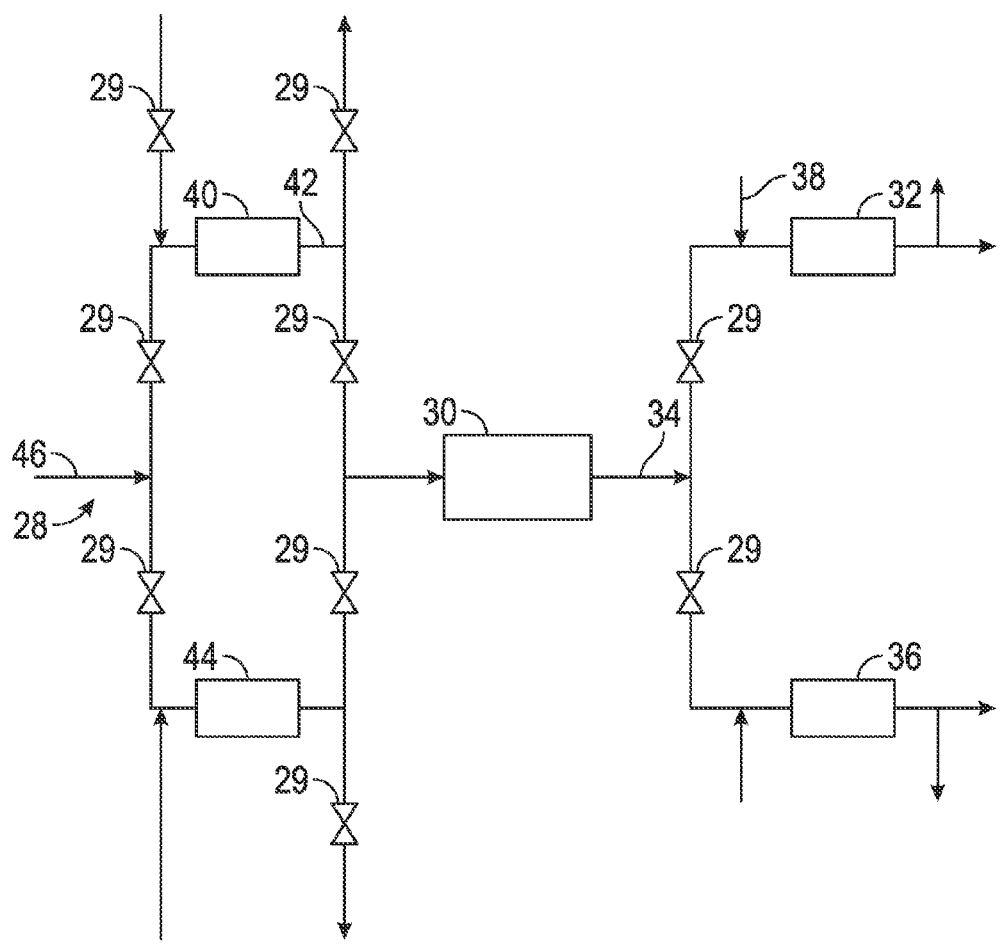
FIG. 3 is a schematic representation of a system in accordance with embodiments disclosed herein.

Referring to FIG. 3, various embodiments are shown of systems and methods comprising COS hydrolysis and $H_2S$ direct oxidation having steam regeneration. In one embodiment, at least one COS hydrolysis reactor 30 may be positioned upstream from at least one direct oxidation reactor 32 to treat $H_2S$ in the product 34 of the COS hydrolysis reactor. The direct oxidation reactor 32 is configured so that flow of the product 34 may be stopped and replaced by steam 38 to regenerate the direct oxidation catalyst. Optionally, one or more second direct oxidation reactors 36 may also be positioned downstream from the COS hydrolysis reactor 30 to enable continuous operation by alternating which direct oxidation reactor 32 or 36 is undergoing steam regeneration.

In another embodiment, a COS hydrolysis reactor 30 may be positioned downstream from a direct oxidation reactor 40 to hydrolyze any COS in the direct oxidation reactor's 40 product 42. The direct oxidation reactor 40 is configured to allow for steam regeneration of the direct oxidation catalyst. Optionally, a second direct oxidation reactor 44 may also be positioned upstream from the COS hydrolysis reactor to allow for alternating steam regeneration between the two or more direct oxidation reactors, i.e. swing bed operation.

In still another embodiment, direct oxidation reactors 32, 40 may be positioned both upstream and downstream of the COS hydrolysis reactor 30. The direct oxidation reactors are configured to allow for steam generation. This arrangement allows for the effective treatment of a gas stream 46 including CO, $H_2S$, and the deposit forming hydrocarbons.

The waste 13 from the steam regeneration process may be handled in a number of ways. In one embodiment, the waste of a direct oxidation reactor undergoing steam regeneration may be fed to another "swing reactor" that is currently performing direct oxidation. In this embodiment, if there is any $H_2S$ in the waste, it may be converted to S by direct oxidation. The outlet of the swing reactor may then be fed to a condenser to condense the steam to water. The water may then be injected into waste injection well or sent to a sour water stripper. In another embodiment, the waste from the steam regeneration process is sent to a condenser and not another direct oxidation reactor. The condensed water may be then be sent to a waste injection well or a sour water stripper.

EXAMPLES

Fouled direct oxidation catalyst was used as the test subject in these experiments. The test catalyst was comprised of titanium dioxide ($TiO_2$), niobium oxide ($Nb_2O_5$) and molybdenum oxide ($MoO_3$). The catalyst is available from SAINT-GOBAIN NORPRO of Stow, Ohio. The test catalyst was fouled by extended exposure to a gas stream containing both $H_2S$ and hydrocarbons. While the exact amounts of the contents of this gas stream would, of course, vary over time, a representative composition in mole % includes 3.69% $H_2$, 65.89% $N_2$, 0.49% $H_2S$, 2.34% CO, 17.84% $CO_2$, 8.00% $CH_4$, 1.21% $C_2H_6$, 0.30% $C_3H_8$, 0.08% C4, 0.03% C5, and 0.14% C6+(C6 hydrocarbons and greater). Prior to regeneration, the fouled test catalyst was observed in the field as being capable of converting only about 60% of $H_2S$ to elemental sulfur at about 230° C. and 15 psig, down from its original >90%.

The fouled direct oxidation catalyst was regenerated with high temperature steam. A 100 g sample of the fouled catalyst was regenerated with steam in a laboratory by slowly increasing the temperature of the catalyst to 330° C. Water was then injected into the preheating zone of the laboratory reactor at rate of about 0.2 ml/min to generate the steam. The steam regeneration process was continued for 10 hours.

Direct oxidation was performed with the steam-regenerated catalyst at 156° C. and atmospheric pressure with a gas hourly space velocity of 1100/hour and a nearly constant $O_2/H_2S$ ratio (0.71-0.74). The steam-regenerated catalyst was observed as converting >90% of the $H_2S$ to elemental sulfur. This conversion rate is comparable to that of fresh, un-fouled catalyst for the same conditions. Fresh direct oxidation catalyst having essentially the same composition was also observed to have >90% conversion at 159° C.

While the invention has been described with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims. Also, while the embodiments included herein are often described with reference to a reactor or other elements in the singular for simplicity, this is not intended to limit the invention. A person of skill in the art would recognize that multiple reactors and other such elements could be utilized where the elements are referred to in the singular.

The invention claimed is:

1. A process for treating a gas stream, the process comprising:
    contacting a gas stream comprising hydrogen sulfide and at least one hydrocarbon component with an oxygen-containing gas in the presence of a direct oxidation catalyst;
    monitoring the amount of sulfur dioxide generated by contacting the gas stream with the direct oxidation catalyst; and
    regenerating the direct oxidation catalyst when the amount of sulfur dioxide reaches a predetermined limit by contacting the direct oxidation catalyst with steam to regenerate the direct oxidation catalyst.

2. The process of claim 1 wherein in the step of contacting the direct oxidation catalyst with steam to regenerate the direct oxidation catalyst comprises:
    contacting the direct oxidation catalyst with mixture comprising steam and oxygen.

3. The process of claim 1 wherein the gas stream is contacted with the oxygen-containing gas in the presence of a direct oxidation catalyst in at least one first reactor.

4. The process of claim 3 wherein the method further comprises: diverting the gas stream to at least one second reactor comprising the direct oxidation catalyst before regenerating the direct oxidation catalyst in the first reactor; and contacting gas stream with the oxygen-containing gas and the direct oxidation catalyst in the second reactor.

5. The process of claim 3 further comprising converting carbonyl sulfide in the gas stream to hydrogen sulfide in at least one first carbonyl sulfide reactor.

6. The process of claim 5 further comprising contacting the gas stream with oxygen in the presence of the direct oxidation catalyst after the gas stream exits the carbonyl sulfide reactor.

* * * * *